(12) United States Patent
Guo

(10) Patent No.: US 7,659,122 B2
(45) Date of Patent: Feb. 9, 2010

(54) SINGLE POPULATION OF SIMULATED LEUKOCYTE GRANULES, CALIBRATORS COMPRISING THE SAME AND METHODS OF PREPARING THE SAME

(75) Inventor: Xiaonan Guo, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 49 days.

(21) Appl. No.: 11/872,522

(22) Filed: Oct. 15, 2007

(65) Prior Publication Data

US 2008/0293145 A1  Nov. 27, 2008

(30) Foreign Application Priority Data

May 24, 2007 (CN) .......................... 2007 1 0106636

(51) Int. Cl.
*G01N 33/48* (2006.01)
*G01N 33/96* (2006.01)

(52) U.S. Cl. .............................. 436/10; 436/8; 436/16; 436/17; 436/18; 436/63; 436/174; 436/175; 435/2

(58) Field of Classification Search ............... 436/8, 436/10, 16, 17, 18, 63, 94, 95, 128, 130, 436/135, 174, 175, 177; 435/2, 14, 29; 252/408.1; 422/73

See application file for complete search history.

(56) References Cited

U.S. PATENT DOCUMENTS

| | | | | |
|---|---|---|---|---|
| 4,704,364 | A | * | 11/1987 | Carver et al. .................... 436/10 |
| 5,262,327 | A | | 11/1993 | Ryan |
| 5,320,964 | A | | 6/1994 | Young et al. |
| 5,672,474 | A | | 9/1997 | Ryan |
| 5,840,515 | A | * | 11/1998 | Provost ........................ 435/29 |
| 5,981,282 | A | * | 11/1999 | Ryan ............................ 436/10 |
| 6,146,901 | A | * | 11/2000 | Carver et al. ................. 436/174 |
| 6,187,590 | B1 | * | 2/2001 | Kim et al. ..................... 436/10 |
| 6,403,377 | B1 | * | 6/2002 | Ryan et al. ..................... 436/8 |
| 6,759,246 | B1 | | 7/2004 | Collins |
| 6,762,055 | B2 | * | 7/2004 | Carver et al. ................... 436/10 |

OTHER PUBLICATIONS

China patent application No. 200710106636.4, Search Report dated Jul. 16, 2007.
BC-5500 Auxiliary Reagent, Cat. No. A12-000141, Mindray Bio-Medical Electronics Co., Ltd, Shenzhen, China.
Rebecca R. Sandborg et al.; "The Effects of Heavy Metal Cations and Sulfhydryl Reagents on Degranulation from Digitonin-Permeabilized Neutrophils"; Biochim Biophys Acta; 1989; pp. 330-337; Elsevier Science Publishers B.V. (Biomedical Division).
Kazuhito Rokutan et al.; "Phagocytosis and Stimulation of the Respiratory Burst by Phorbol Diester Initiate S-Thiolation of Specific Proteins in Macrophages"; The Journal of Immunology; Jul. 1, 1991; pp. 260-264; vol. 147; The American Association of Immunologists.
Yuh-Cherng Chai et al.; "S-Thiolation of Individual Human Neutrophil Proteins Including Actin by Stimulation of the Respiratory Burst: Evidence Against a Role for Glutathione Disulfide"; Archives of Biochemistry and Biophysics; Apr. 1994; pp. 272-281; vol. 310, No. 1; Academic Press, Inc.
"Reference Method for the Enumeration of Erythrocytes and Leucocytes"; International Council for Standardization in Haematology; Prepared by the Expert Panel on Cytometry; Clin. Lab. Haematol; Jun. 1994; pp. 131-138.

* cited by examiner

*Primary Examiner*—Maureen M Wallenhorst
(74) *Attorney, Agent, or Firm*—Vista IP Law Group, LLP.

(57) ABSTRACT

Disclosed is a single population of simulated leukocyte granules prepared from mammalian whole white blood cells, which is useful in calibrators for a hematology analyzer, a calibrator which includes the single population of simulated leukocyte granules. Disclosed is also a method of preparing the single population of simulated leukocyte granules. The method of preparing single population of simulated leukocyte granules includes the actions of: obtaining mammalian whole white blood cells; treating the mammalian whole white blood cells with a hemolytic agent and a leukocyte treating liquid which includes an isotonic saline solution. The isotonic saline solution may include a fixative, an oxidizer, and a carbohydrate compound; fixing the treated mammalian whole white blood cells with a fixative; and suspending the fixed cells in a preservation medium for long-term preservation of fixed cells.

13 Claims, 3 Drawing Sheets

US 7,659,122 B2

SINGLE POPULATION OF SIMULATED LEUKOCYTE GRANULES, CALIBRATORS COMPRISING THE SAME AND METHODS OF PREPARING THE SAME

STATEMENT OF RELATED APPLICATION

This application claims the benefit of priority to China Patent Appl. No. 200710106636.4, filed on May 24, 2007, entitled "Single Population of Simulated Leukocyte Granules, Calibrators Comprising the Same and Methods of Preparing the Same", which is hereby incorporated by reference.

FIELD OF THE INVENTION

The present invention relates to the field of hematology analysis, and more specifically, to single population of simulated leukocyte granules prepared from mammalian whole white blood cells, calibrators comprising the same and methods of preparing the same.

BACKGROUND OF INVENTION

A hematology analyzer has been usually calibrated before it leaves factory. However, it is possible that its scales of measurement will be drifted when being transported and used, and therefore, the analyzer needs to be calibrated. Calibration parameters of a hematology analyzer include white blood cell (leukocyte, WBC), red blood cell (erythrocyte, RBC) and platelet (PLT) counts, hemoglobin (HGB), mean corpuscular volume (MCV), and hematocrit (HCT). Methods for determining the reference value of these parameters may refer to respective international standard methods. With reference to white blood cells (WBC), according to international reference methods (See, e.g., Clin Lab Haematol., 1994 June; 16(2):131-8), it is only possible to obtain a total white blood cell count, but not possible to achieve leukocyte differentiation. In case of calibrators for various hematology analyzers, it is sufficient that the leukocyte components of calibrators are a single population of granules rather than simulated granules of differential leukocytes (classes of leucytes).

There are many methods of preparing single population of simulated leukocyte granules described in prior art. These methods may be classified as follows: 1) preparing simulated granules of non-cellular origin from pollen, latex particle and the like; 2) treating animal erythrocytes to simulate leukocytes; 3) treating mammalian granulocytes to simulate certain class of leukocytes. These processed single population of simulated leukocyte granules are primarily used to prepare some control products. Although the prior art gives no word to the simulation of leukocyte component for use in calibrators, in fact, the processing methods used are totally applicable to the preparation of simulated leukocyte granules for use in calibrators.

Due to insurmountable defects in cost, compatibility of instrument system and the like, simulated granules of non-cellular origin have been gradually taken over by processed cell-derived granules. For example, based on the original volume of cells, different single populations of simulated leukocyte granules can be obtained by treating animal erythrocytes. U.S. Pat. No. 4,704,364 discloses that human lymphocytes are simulated with human erythrocytes, human monocytes are simulated with turkey erythrocytes, and human granulocytes are simulated with erythrocytes of a shark species. U.S. Pat. No. 5,320,964 discloses that human lymphocytes are simulated with avian nucleated red blood cells, and human monocytes, neutrophils, eosinophils are simulated with red blood cells of reptiles. In accordance with these methods, single population of simulated leukocyte granules are obtained by harvesting animal erythrocytes by centrifugation and fixing them using aldehyde compounds. Such single population of simulated leukocyte granules exhibits good suspensibility and stability, and can be used to simulate leukocyte components for used in control products or calibrators of some hematology analyzers.

There are detailed descriptions for methods of treating mammalian granulocytes in U.S. Pat. No. 6,759,246. By treating granulocytes of swine, cattle and other suitable mammals with reagents such as Bronopol and Triadine-3, granulocytes become similar to human lymphocytes in properties of light scatter, impedance, conductivity and dye uptake, whereby they are identified as lymphocytes on some hematology analyzers. Then, the simulated lymphocytes are fixed using aldehyde reagents as a cell fixative. This patent discloses that compared with human lymphocytes simulated with mammalian lymphocytes, human lymphocyte analogs simulated with granulocytes show greater stability in cell volume on a analyzer. Furthermore, analogs of single population of neutrophils and eosinophils may be also simulated with processed porcine granulocytes, while analogs of single population of monocytes come from processing bovine granulocytes.

However, the prior art methods of preparing analogs of single population of leukocytes still suffer from some drawbacks. When some single population of human leukocyte granules simulated with animal red blood cells are detected on a hematology analyzer using impedance method, a standard histogram distribution of human leukocytes from fresh blood is exhibited (See FIG. 1). Nevertheless, in case of 5-part differential hematology analyzer based on forward light scatter, side light scatter, etc., the scatter plot exhibited by single population of leukocytes which is simulated with animal nucleated red blood cells does not show the distributional characteristics of single population clusters (See FIG. 2), because animal nucleated red blood cells generally have an ellipse rather than a spherical shape. Cells are passed through flow chamber in various "postures", resulting in nonuniform light scatter properties, for example, sector trailing distribution or complete dispersionas shown in FIG. 2. Although lymphocytes simulated with mammalian granulocytes or other single population of leukocytes can be used for 5-part differential hematology analyzer based on multi-angle light scatter, it requires granulocytes being separated, for example, by separation methods such as density gradient, and moreover special treatment and prolonged fixation. Therefore, these methods are not desirable due to complexity.

To overcome the poor clustering subjected to the leukocyte granules simulated with animal red blood cells, and complexity in processing regarding the single population of leukocytes simulated with animal granulocytes, the present invention provides a method of preparing single population of simulated leukocyte granules, adapted for calibrators of a hematology analyzer employing a multi-angle light scatter theory (e.g., 5-part differential hematology analyzer), which method is simple in operation, has low cost and good granule clustering, and exhibit excellent stability.

SUMMARY OF THE INVENTION

According to one embodiment of the present invention, there is provided a method of preparing single population of simulated leukocyte granules, comprising the steps of:

(1) obtaining mammalian whole white blood cells;

(2) treating the mammalian whole white blood cells under the action of a hemolytic agent in the presence of a leukocyte treating liquid, i.e., an isotonic saline solution comprising a fixative, a oxidizer and a carbohydrate;

(3) fixing the treated mammalian whole white blood cells with a fixative after washing the treated cells; and (4) suspending the fixed cells in a preservation medium suitable for long-term preservation of fixed cells.

In a further embodiment of the present invention, said mammalian whole white blood cells are obtained by mixing mammalian fresh whole blood with a hemolytic agent to lyse erythrocytes thereof. A leukocyte treating liquid may be added directly to the mixture for treatment.

According to another embodiment, the present invention provides a single population of simulated leukocyte granules prepared from mammalian whole white blood cells, preferable prepared using the above methods.

In a still another embodiment, the present invention relates to a calibrator comprising the above-mentioned single population of simulated leukocyte granules.

Further features and advantages of the present invention will be more apparent from the following description with reference to the accompanying drawings.

DETAILED DESCRIPTION OF THE INVENTION

Figure 1:
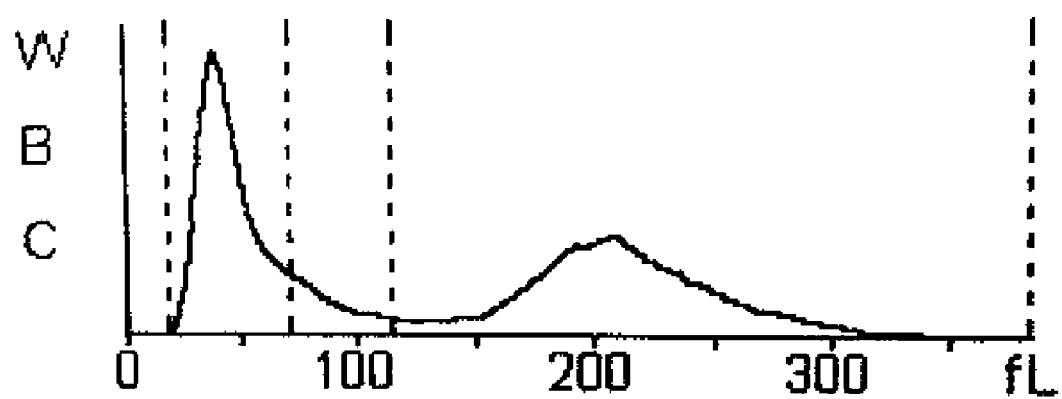
FIG. 1 is a histogram showing different classes of leukocytes simulated with different animal nucleated red blood cells analyzed on a hematology analyzer using impedance method, which is consistent with the distribution of human leukocytes.
Figure 2A:
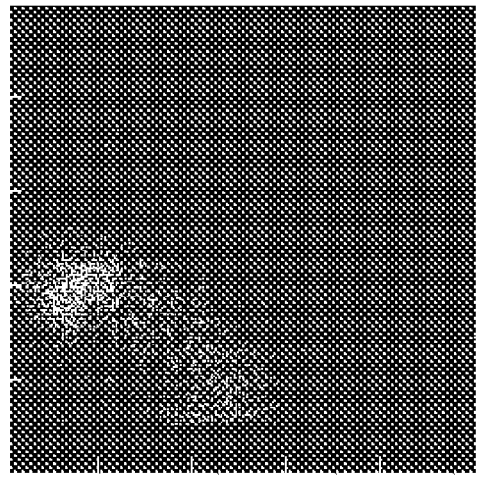
FIG. 2 (2a, 2b) is a scatter plot showing different classes of leukocyte simulated with different animal nucleated red blood cells analyzed on a 5-part differential hematology analyzer BC-5500 (Mindray Bio-Medical Electronics Co., Ltd, Shenzhen, China). There is not boundary between the simulated leukocytes and cell debris, exhibiting a poor clustering.
Figure 2B:
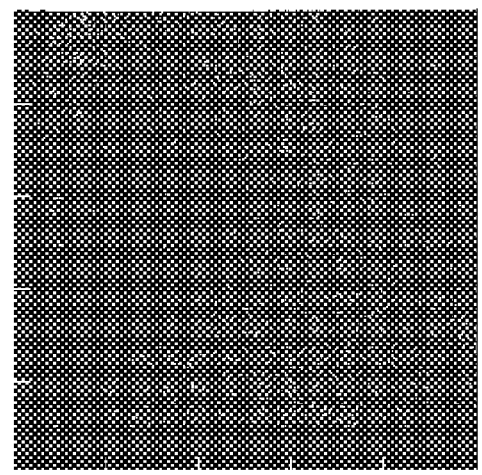

In the specification, unless otherwise specified, the singular forms "a", "an", and "the" include the corresponding plural reference. Thus, for example, a reference to "a fixative" includes a plurality of fixatives.

The term "whole white blood cells" as used herein refers to all types of white blood cells present in the peripheral blood, which include lymphocytes, monocytes, neutrophils, eosinophils, basophils and the like. This term includes those whole white blood cells that are prepared by treating mammalian fresh whole blood with a hemolytic agent to remove erythrocytes therein, and those prepared with otherwise methods, for example, the whole white blood cells which are prepared by treating buffy coat layer with a hemolytic agent (See U.S. Pat. No. 6,187,590 B1, the patent is hereby incorporated by reference).

The term "a single population of simulated leukocyte granules" as used herein means that the granules have uniform light scatter property so that they are identified as a single population of leukocytes on a multi-angle light scatter based hematology analyzer.

The term "hemolytic agent" as used herein includes any substance that can lyse erythrocytes in the blood, as long as it can achieve the object of the present invention, for example, a conventional or commercially available hemolytic agent which contains cationic, anionic, non-ionic or ampholytic surfactant as an active ingredient.

The term "fixative" as used herein refers to any substance which can be used to fix cells, for example, aldehyde compounds such as paraformaldehyde, formaldehyde, acetaldehyde, glyoxal, glutaraldehyde and the like, or mixture of these fixatives.

The term "isotonic solution" as used herein includes any solution which is isotonic with blood, such as, conventional isotonic phosphate solution, isotonic sodium chloride solution and the like.

As described above, since the scales of measurement of a hematology analyzer may be drifted during transport and usage, the hematology analyzer needs to be calibrated. According to the international standard methods for determining calibration parameters of a hematology analyzer (See, e.g., Clin Lab Haematol., 1994 June; 16(2):131-8), it is only possible to obtain a total white blood cell count, but not leukocyte differentiation. In case of calibrators for various hematology analyzers, it is sufficient that the leukocyte components of calibrators are a single population of granules rather than simulated granules of differential leukocytes.

The inventor has discovered that since leukocytes are shrinked to a different extent by a hemolytic agent, by treating whole white blood cells of a mammal (for example, swine, sheep, cattle and other suitable animal) with a hemolytic agent in the presence of an isotonic saline solution comprising a fixative, a oxidizer and a carbohydrate, the volume of various classes of leukocytes can be adjusted to minimize the volume difference between leukocytes, such that the leukocytes tend to have uniform volume and light scatter properties. Whereby, single population of simulated leukocyte granules suitable for calibrators of a multi-angle light scatter based hematology analyzer (for example, 5-part differential hematology analyzer) can be conveniently prepared from mammalian whole white blood cells, without separation of certain class of leukocytes.

Therefore, the present invention provides a method of preparing single population of simulated leukocyte granules for use in calibrators of a hematology analyzer, said method comprising treating the mammalian whole white blood cells under the action of a hemolytic agent in the presence of an isotonic saline solution comprising a fixative, a oxidizer and a carbohydrate.

Acquisition of Mammalian Whole White Blood Cells

The mammalian whole white blood cells can be prepared by mixing mammalian fresh whole blood with a hemolytic agent to lyse erythrocytes therein. For example, mammalian fresh whole blood is collected using EDTA isotonic saline solution (e.g., 0.9% NaCl solution containing 4% EDTA) as an anticoagulant agent, and stored for 0-5 days at 4° C. The processing method may be varied with a longer preservation.

A suitable hemolytic agent is selected, for example, a conventional or commercially available hemolytic agent which contains as an active component cationic, anionic, non-ionic or ampholytic surfactant, and combined with a amount of mammalian whole white blood cells. A suitable amount, temperature and time are determined depending upon different types of hemolytic agents. The volume ratio of the hemolytic agent to the mammalian fresh whole blood is about 2:1 to about 12:1, for example, about 2:1 to about 10:1; the treating time may be about 1 to about 25 minutes, for example, about 1 minutes to about 20 minutes. With reference to a mild hemolytic agent (e.g., 0.748% NH$_4$Cl, 0.26% Tris, and 0.025% Saponin), the amount of hemolytic agent may be increased, or the treating time may be prolonged, for example, the volume ratio of the hemolytic agent to the mammalian fresh whole blood is about 3:1 to about 12:1, preferably about 3:1 to about 10:1, such as 4:1, 5:1, 6:1, 7:1, 8:1 or 9:1; the treating time is about 3 minutes to about 25 minutes, preferably about 5 minutes to about 20 minutes, such as about 10 minutes to about 15 minutes. In case of a stronger hemolytic agent, for example, a commercially available hemolytic agent M-50LEO(I) (BC-5500 auxiliary reagent, Cat. No. A12-000141, Mindray Bio-Medical Electronics Co., Ltd, Shenzhen, China), the treating time may be reduced and/or the amount of the hemolytic agent decreased, for example, the volume ratio of the hemolytic agent to mammalian fresh whole blood is about 2:1 to about 8:1; the treating time is about 60 seconds to about 5 minutes, such as, 1, 2, 3, 4 and 5 minutes, preferably about 1 minute to about 3 minutes. The suitable amount and treating time of the hemolytic agent are readily selected by one skilled in the art based on the prior art techniques for removing erythrocyte from whole blood with a hemolytic agent. During this period, as leukocyte is shrinked by the hemolytic agent, the volume of various classes of leukocytes can be preliminarily adjusted to reduce the volume difference between the leukocytes.

The mammalian whole white blood cells can be also obtained by other methods, for example, treating a buffy coat layer with a hemolytic agent (See U.S. Pat. No. 6,187,590 B1).

Modulation of the Volume and Light Scatter Properties of the Whole White Blood Cells A leukocyte treating liquid, i.e., an isotonic saline solution comprising a suitable amount of a fixative, a oxidizer and a carbohydrate, is added to the above mentioned hemolytic mixture, where the whole white blood cells is kept being treated. The treating temperature may be, for example, controlled within 10° C.-30° C.; the treating time may be, for example, about 10 minutes to about 60 minutes, for example, about 15, 20, 25, 30, 35, 40, 45 or 55 minutes. The hemolytic agent was diluted by the isotonic saline solution comprising the above various components to a suitable proportion, for example, the volume ratio of the leukocyte treating liquid to the hemolytic mixture is 0.5:1-5:1, such as about 1:1, 2:1, 3:1 or 4:1, preferably about 1:1 to about 3:1. The hemolytic agent may continuously lyse erythrocytes and decrease the volume difference of various classes of leukocytes. If the whole white blood cells are obtained without having been treated with a hemolytic agent, a suitable amount of hemolytic agent can be added, for example, the hemolytic agent may account for about 15% (v/v) to about 60% (v/v) of the whole mixture.

The fixative in the leukocyte treating liquid can include an aldehyde compound, such as, paraformaldehyde, formaldehyde, acetaldehyde, glyoxal, glutaraldehyde and the like, or a mixture of these fixatives. Concentration of the fixatives can be determined depending upon specific fixatives using the prior art method, for example, the final concentration is about 0.002%-5% (v/v). One skilled in the art will appreciate that the amount of the fixative should be controlled within a appropriate range, because if the concentration is excessively high, residual erythrocytes, if any, would be partially fixed; and if the concentration is excessively low, partial leukocytes may be lysed to debris by the hemolytic agent.

The oxidant in the leukocyte treating liquid mainly include oxidants which act on the sulfhydryl group of some intracellular proteases, such as diamide, H$_2$O$_2$, pervanadate and the like. It is reported that oxidization of the sulfhydryl group in leukocytes may involve in signal transduction of the cells, and the sulfhydryl group is oxidized to a disulfide bond, thus considerably stimulating neutrophils to release enzyme granules, which is useful in reducing complexity of granulocyte granules (See, e.g., Sandborg R R and Smolen J E. "The effects of heavy metal cations and sulfhydryl reagents on degranulation from digitonin-permeabilized neutrophils." Biochim Biophys Acta. 1989 Mar. 6; 1010(3):330-7; Rokutan K et al., "Phagocytosis and stimulation of the respiratory burst by phorbol diester initiate S-thiolation of specific proteins in macrophages." J Immunol. 1991 Jul. 1; 147(1):260-4; and Chai Y C et al., "S-thiolation of individual human neutrophil proteins including actin by stimulation of the respiratory burst: evidence against a role for glutathione disulfide." Arch Biochem Biophys, 1994 April; 310(1):273-81). The oxidant of the present invention is mainly useful to change light scatter intensity of mammalian granulocytes, reduce difference in complexity of granulocytes and lymphocytes, monocytes, whereby reducing difference in light scatter properties thereof. The amount of the oxidants may be determined depending upon the specific oxidant used, for example, the final concentration of H$_2$O$_2$ is about 0.01% to about 0.1% (v/v), and the final concentration of diamide is about 0.2 mM to about 0.6 mM.

The carbohydrate involved in the leukocyte treating liquid can include a monosaccharide or disaccharide, such as, glucose, galactose, saccharose, lactose, mannitol and the like, and can be used to modulate the osmotic pressure of the reactive system and maintain light scatter properties of leukocytes. The final concentration of the carbohydrate is usually about 0.5% to about 3% (v/v), and any other suitable final concentration is also applicable.

Fixation and Preservation of Whole White Blood Cells

After lysing erythrocytes and modulating volume and light scatter properties of the whole white blood cells, the processed whole white blood cells can be fixed according to conventional methods and preserved in a suitable preservation medium.

For example, after lysing erythrocytes and modulating volume and light scatter properties of the whole white blood cells, the whole white blood cells can be collected by centrifugation. The hemolytic mixture is replaced with a isotonic saline solution, and the cells are fixed with suitable concentration of a aldehyde fixative, for example, formaldehyde with final concentration of about 4% to about 10% (v/v), or glutaraldehy with final concentration of about 0.1% to about 1.0% (v/v). The fixation time can be controlled within 30-120 minutes, the fixation temperature within 10° C.-30° C. If the temperature is increased, the fixation time may be properly reduced. On the contrary, the fixation time may be prolonged.

The simulated leukocyte granules are washed with an isotonic saline solution by centrifugation to thoroughly remove the residual fixative, platelets and erythrocyte debris. Finally, the fixed single population of simulated leukocyte granules are suspended in a preservation medium. Under the circumstance that it is required to form a whole blood calibrator, the granules are then combined with erythrocytes and platelets in a suitable proportion.

The methods according to the present invention are superior in its simplicity, because mammalian whole white blood cells are directly treated, without separation of an individual class of cell for treatment and fixation. Therefore, a complex separation is avoided, thus reducing losses in cells occurring in the separation. At the same time, the time necessary for fixation is remarkably shortened, without compromising the stability of the granules. Another advantage of the present invention is cost-efficient. The mammalian whole white blood cells prepared with such methods not only exhibit desirable clustering, but also have low cost due to a rich source of materials.

The present invention further provides a single population of simulated leukocyte granules prepared according to the above mentioned methods of the present invention.

The present invention further provides a calibrator containing the single population of simulated leukocyte granules according to the present invention. The calibrator according to the present invention can be used in a multi-angle light scatter based hematology analyzer, for example, a 5-part differential hematology analyzer.

The invention will now be further described with reference to the non-limiting examples below.

EXAMPLES

Example 1

Porcine fresh whole blood was collected in the presence of an anticoagulant, containing RBC from 3.0-8.0 $\times 10^{12}$/L, and WBC from 10.0-40.0 $\times 10^9$/L as measured. 1V (volume) fresh whole blood was mixed with 8V commercially available hemolytic agent M-50LEO(I) (BC-5500 auxiliary reagent, Cat. No. A12-000141, Mindray Bio-Medical Electronics Co., Ltd, Shenzhen, China) for 3 minutes. 9V leukocyte treating liquid was added, which was isotonic saline solution (0.9% NaCl solution) containing 6% formaldehyde, 0.06% $H_2O_2$ and 2% lactose. The mixture was held at room temperature for 30 minutes. After centrifugation, the supernatant was discarded. The white blood cells was subsequently washed five times with 0.9% NaCl solution by centrifugation, and the whole WBC pellets were collected. The whole WBCs were resuspended in isotonic NaCl solution containing glutaraldehyde with final glutaraldehyd concentration of 0.2%, and fixed at room temperature for 30 minutes. At last, the white blood cells were washed 3-5 times with 0.9% NaCl solution. The washed simulated leukocyte granules were finally suspended in a preservation mediumand stored at 4° C.

Example 2

Porcine fresh whole blood was collected in the presence of an anticoagulant, containing RBC from 3.0-8.0 $\times 10^2$/L, and WBC from 10.0-40.0 $\times 10^9$/L as measured. 1V (volume) fresh whole blood was mixed with 5V hemolytic agent (0.748% $NH_4Cl$, 0.26% Tris, 0.025% saponin) for 15 minutes. 6V leukocyte treating liquid which was isotonic saline solution containing 0.005% glutaraldehyd, 0.6 mM diamide and 2% lactose, was added at room temperature for 40 minutes. After centrifugation, the supernatant was discarded. The white blood cells was subsequently washed 5 times with 0.9% NaCl solution by centrifugation, and the whole WBC pellet was collected. The whole WBCs were resuspened in a isotonic NaCl solution containing glutaraldehyde with final glutaraldehyde concentration of 0.3%, and fixed at room temperature for 20 minutes. At last, the white blood cells were washed 3-5 times with 0.9% NaCl solution by centrifugation. The washed leukocyte simulated granule were finally suspended in a preservation medium and stored at 4° C.

Results

Figure 3:
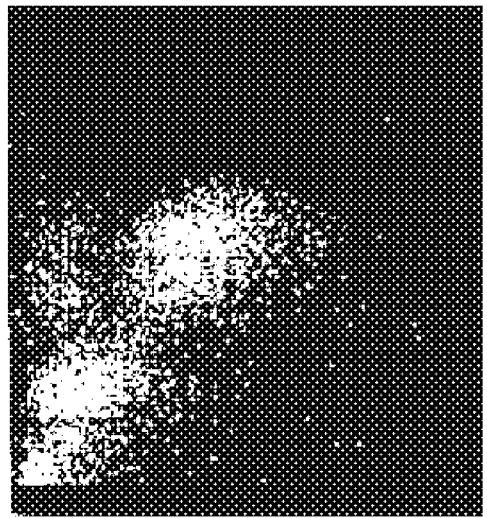
FIG. 3 is a scatter plot of porcine fresh leukocytes in a DIFF channel of the 5-part differential hematology analyzer BC-5500, and the porcine fresh leukocytes were identified by the instrument as different populations of WBC.
Figure 4:
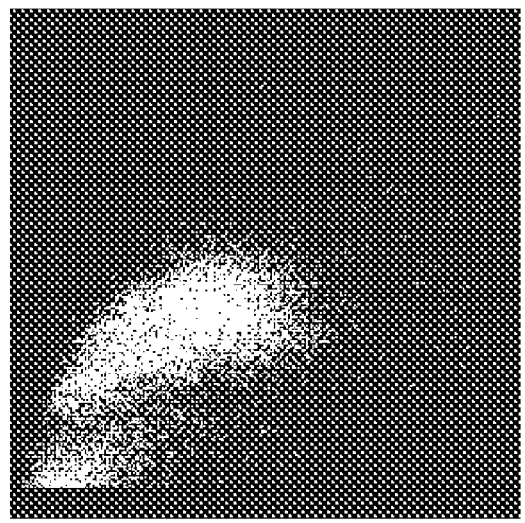
FIG. 4 shows a scatter plot of porcine whole white blood cells processed using the method of Example 1 in the DIFF channel of the 5-part differential hematology analyzer BC-5500. It is found that there is boundary between the processed leukocytes and cell debris, representing a single population clustering distribution.

The single population of simulated leukocyte granules obtained according to the methods provided in the above Examples was analyzed on 5-part differential hematology analyzer BC-5500. FIG. 3 shows a scatter plot of porcine fresh leukocytes in the DIFF channel of a BC-5500 5-part differential hematology analyzer, and the porcine fresh leukocytes were identified by the instrument as different populations of WBC. FIG. 4 shows a scatter plot of porcine whole white blood cells processed with the method of Example 1 in the DIFF channel of BC-5500, 5-part differential hematology analyzer. Compared with the scatter plot of the porcine whole white blood cells, there are boundary between the processed leukocytes and cell debris, representing a single population clustering distribution. Result of the other example is similar with that of Example 1.

It can be seen from above that light scatter properties of mammalian whole white blood cells after processed using the methods according to the present invention tend to be uniform. These mammalian whole white blood cells are processed into single population of simulated leukocyte granules with uniform light scatter performance, which ultimately exhibits a clustering single population distribution on a scatter plot of 5-part differential hematology analyzer, for example, the BC-5500.

Furthermore, the single population of simulated leukocyte granules prepared by the methods according to the present invention still maintain their light scatter properties after being stored for 90 days at 4° C. This suggests that their stability satisfies the requirements for leukocyte component granules of calibrators.

Although the present invention has been described in accordance with the particular embodiments as described above, one skilled in the art will recognize that the present invention is not limited to these particular embodiments. Modifications and improvements can be made to particular embodiments of the invention without departing from the spirit and scope of the present invention. These equivalent embodiments will be included in the scope of the invention.

What is claimed is:

1. A method of preparing a single population of simulated leukocyte granules, comprising:
   obtaining mammalian whole white blood cells;
   treating the mammalian whole white blood cells by combining the mammalian whole white blood cells with at least a hemolytic agent and a leukocyte treating liquid comprising an isotonic saline solution, wherein the isotonic saline solution comprises a fixative, an oxidizer, and a carbohydrate compound;
   washing the treated mammalian whole white blood cells;
   after the act of treating and washing the mammalian whole white blood cells, fixing the mammalian whole white blood cells with a fixative; and
   after the act of fixing the mammalian whole white blood cells, suspending the mammalian whole white blood cells in a preservation medium for long-term preservation of the mammalian whole white blood cells.

2. The method of claim 1, wherein the mammalian whole white blood cells are obtained by mixing mammalian fresh whole blood with a hemolytic agent to lyse erythrocytes thereof.

3. The method of claim 2, wherein the leukocyte treating liquid is added to a mixture of the mammalian fresh whole blood and the hemolytic agent for treatment.

4. The method of claim 3, wherein a ratio of the leukocyte treating liquid to the mixture of the mammalian fresh whole blood and the hemolytic agent is about 0.5:1 to about 5:1.

5. The method of claim 4, wherein the ratio of the leukocyte treating liquid to the mixture is about 1:1 to about 3:1.

6. The method of claim 2, wherein a ratio of the hemolytic agent to the mammalian fresh whole blood is 2:1 to 12:1.

7. The method of claim 6, wherein the ratio of the hemolytic agent to the mammalian fresh whole blood is about 2:1 to about 10:1.

8. The method according to claim 1, wherein the fixative in the leukocyte treating liquid is an aldehyde fixative.

9. The method of claim 8, wherein the aldehyde fixative is selected from the group consisting of paraformaldehyde, formaldehyde, acetaldehyde, glyoxal and glutaraldehyde.

10. The method of claim 8, wherein the aldehyde fixative in the leukocyte treating liquid has a final concentration of about 0.002% to about 5% (v/v).

11. The method according to claim 1, wherein the oxidizer oxidizes a sulfhydryl group of an intracellular protease.

12. The method of claim 11, wherein said oxidizer is selected from a group consisting of diamide, $H_2O_2$ and pervanadic acid.

13. The method according to claim 1, wherein said carbohydrate is selected from a group consisting of glucose, galactose, sucrose, lactose, and mannitol.

* * * * *